(12) United States Patent
Cheng

(10) Patent No.: US 9,345,386 B1
(45) Date of Patent: May 24, 2016

(54) ADJUSTABLE ENDOSCOPE SHEATH

(71) Applicant: Gyrus ACMI, Inc., Southborough, MA (US)

(72) Inventor: Ming J. Cheng, W. Warwick, RI (US)

(73) Assignee: GYRUS ACMI, INC., Southborough, MA (US)

( * ) Notice: Subject to any disclaimer, the term of this patent is extended or adjusted under 35 U.S.C. 154(b) by 0 days.

(21) Appl. No.: 14/551,208

(22) Filed: Nov. 24, 2014

(51) Int. Cl.
*A61B 1/00* (2006.01)
*A61B 1/015* (2006.01)
*A61B 1/12* (2006.01)

(52) U.S. Cl.
CPC ......... *A61B 1/00135* (2013.01); *A61B 1/00128* (2013.01); *A61B 1/015* (2013.01); *A61B 1/126* (2013.01)

(58) Field of Classification Search
USPC .......................... 600/114, 117–118, 121–125
See application file for complete search history.

(56) References Cited

U.S. PATENT DOCUMENTS

| | | | |
|---|---|---|---|
| 4,188,942 A * | 2/1980 | Fehlberg | A61B 1/00105 285/305 |
| 4,254,762 A | 3/1981 | Yoon | |
| 4,281,646 A | 8/1981 | Kinoshita | |
| 4,312,375 A | 1/1982 | Leinemann | |
| 4,548,197 A | 10/1985 | Kinoshita | |
| 4,646,722 A | 3/1987 | Silverstein et al. | |
| 5,170,774 A | 12/1992 | Heckele | |
| 5,176,645 A | 1/1993 | Guerrero | |
| 5,178,606 A | 1/1993 | Ognier et al. | |
| 5,199,417 A | 4/1993 | Muller et al. | |
| 5,207,213 A | 5/1993 | Auhll et al. | |
| 5,237,984 A | 8/1993 | Williams et al. | |
| 5,269,756 A | 12/1993 | Dryden | |
| 5,306,272 A * | 4/1994 | Cohen | A61B 19/201 403/370 |
| 5,313,934 A | 5/1994 | Wiita et al. | |
| 5,354,267 A | 10/1994 | Niermann et al. | |
| 5,413,092 A | 5/1995 | Williams, III et al. | |
| 5,419,309 A | 5/1995 | Biehl | |
| 5,439,022 A | 8/1995 | Summers et al. | |
| 5,486,155 A | 1/1996 | Muller et al. | |

(Continued)

FOREIGN PATENT DOCUMENTS

EP 0374727 A1 6/1990
JP H05/038323 A 2/1993

(Continued)

OTHER PUBLICATIONS

Potentially Related U.S. Appl. No. 14/497,815, dated Sep. 26, 2014.

(Continued)

*Primary Examiner* — Matthew J Kasztejna
(74) *Attorney, Agent, or Firm* — The Dobrusin Law Firm, P.C.

(57) ABSTRACT

An endoscope sheath is providing comprising a sheath tube extending along a longitudinal axis between a proximal end and a distal end, the sheath tube configured to receive at least a portion of an endoscope; a hub adapter connected to the sheath tube, the hub adapter including an arm configured to engage at least a portion of the endoscope so that the hub adapter and the sheath tube are restricted from rotating about the longitudinal axis; and a knob configured to engage a shoulder of the endoscope and the sheath tube so that movement of the knob relative to the hub adapter moves the sheath tube axially along the longitudinal axis.

20 Claims, 3 Drawing Sheets

(56) References Cited

U.S. PATENT DOCUMENTS

| | | | |
|---|---|---|---|
| 5,505,707 A | 4/1996 | Manzie et al. | |
| 5,551,448 A | 9/1996 | Matula et al. | |
| 5,554,112 A | 9/1996 | Walbrink et al. | |
| 5,556,258 A | 9/1996 | Lange et al. | |
| 5,575,756 A | 11/1996 | Karasawa et al. | |
| 5,630,795 A | 5/1997 | Kuramoto et al. | |
| 5,695,448 A * | 12/1997 | Kimura | A61B 1/0005 600/114 |
| 5,797,836 A | 8/1998 | Lucey et al. | |
| 5,989,183 A | 11/1999 | Reisdorf et al. | |
| 6,004,263 A * | 12/1999 | Nakaichi | A61B 1/800165 600/120 |
| 6,110,103 A | 8/2000 | Donofrio | |
| 6,126,592 A | 10/2000 | Proch et al. | |
| 6,181,442 B1 | 1/2001 | Ogura et al. | |
| 6,196,967 B1 * | 3/2001 | Lim | A61B 1/00128 600/125 |
| 6,282,442 B1 | 8/2001 | DeStefano et al. | |
| 6,354,813 B1 | 3/2002 | Laing | |
| 6,447,446 B1 | 9/2002 | Smith et al. | |
| 6,478,731 B2 | 11/2002 | Speier et al. | |
| 6,558,379 B1 | 5/2003 | Batchelor et al. | |
| 6,652,484 B1 | 11/2003 | Hunckler et al. | |
| 7,252,110 B2 | 8/2007 | Semeia | |
| 7,270,647 B2 | 9/2007 | Karpowicz et al. | |
| 7,413,542 B2 | 8/2008 | Kucklick et al. | |
| 7,708,689 B2 | 5/2010 | Deppmeier et al. | |
| 7,811,228 B2 | 10/2010 | Adams | |
| 7,927,271 B2 * | 4/2011 | Dimitriou | A61B 1/00128 600/104 |
| 8,001,984 B2 | 8/2011 | Sasaki | |
| 8,047,215 B1 | 11/2011 | Sasaki | |
| 8,079,952 B2 | 12/2011 | Fujimoto | |
| 8,231,574 B2 | 7/2012 | Haack et al. | |
| 8,337,470 B2 | 12/2012 | Prasad et al. | |
| 8,394,013 B2 | 3/2013 | Ichimura | |
| 8,419,624 B2 | 4/2013 | James et al. | |
| 9,050,037 B2 * | 6/2015 | Poll | A61B 1/00091 |
| 2002/0120180 A1 | 8/2002 | Speier et al. | |
| 2004/0073088 A1 | 4/2004 | Friedman et al. | |
| 2005/0025646 A1 | 2/2005 | Miller et al. | |
| 2006/0041186 A1 | 2/2006 | Vancaillie | |
| 2006/0199998 A1 | 9/2006 | Akui et al. | |
| 2006/0264995 A1 | 11/2006 | Fanton et al. | |
| 2007/0149993 A1 * | 6/2007 | Kasahara | A61B 17/00008 606/190 |
| 2007/0213668 A1 | 9/2007 | Spitz | |
| 2008/0072970 A1 | 3/2008 | Gasser et al. | |
| 2008/0081948 A1 | 4/2008 | Weisenburgh et al. | |
| 2008/0200764 A1 | 8/2008 | Okada | |
| 2009/0234193 A1 | 9/2009 | Weisenburgh, Ii et al. | |
| 2009/0244223 A1 | 10/2009 | Mizutani et al. | |
| 2010/0198012 A1 | 8/2010 | Poole et al. | |
| 2011/0230716 A1 | 9/2011 | Fujimoto | |
| 2012/0316394 A1 | 12/2012 | Yoshida et al. | |
| 2013/0205936 A1 | 8/2013 | Schmieding et al. | |
| 2013/0211433 A1 | 8/2013 | Kadykowski et al. | |
| 2013/0289595 A1 | 10/2013 | Edwards et al. | |

FOREIGN PATENT DOCUMENTS

| | | |
|---|---|---|
| JP | H06/189893 A | 7/1994 |
| JP | 2005/040184 A | 2/2005 |
| JP | 2012/045325 A | 3/2012 |
| WO | 02/33296 A2 | 4/2002 |
| WO | 2012/069592 A1 | 5/2012 |

OTHER PUBLICATIONS

Potentially Related U.S. Appl. No. 14/493,581, dated Sep. 23, 2014.
Potentially Related U.S. Appl. No. 14/496,473, dated Sep. 25, 2014.
Potentially Related U.S. Appl. No. 14/493,700, dated Sep. 23, 2014.
Potentially Related U.S. Appl. No. 14/551,440, dated Nov. 24, 2014.
Potentially Related U.S. Appl. No. 14/592,397, dated Jan. 8, 2015.
US 5,772,579, 06/1998, Reisdorf et al. (withdrawn)

* cited by examiner

ADJUSTABLE ENDOSCOPE SHEATH

FIELD

The present teachings generally relate to an endoscope sheath and more specifically to an endoscope sheath that is moveable relative to an endoscope.

BACKGROUND

Some endoscope sheaths include one or more features for cleaning a distal viewing end of an endoscope. To function properly, these features may require that a distal end the endoscope sheath be axially aligned with the distal viewing end of the endoscope. In this regard, if an endoscope sheath is too short, for example, the distal end of the endoscope sheath may not reach the distal viewing end of the endoscope, and may be prevented from properly cleaning the endoscope. If an endoscope sheath is too long, however, the distal end of the endoscope sheath may interfere with the distal viewing end of the endoscope and may compromise visual access into an internal location of a patient. A long endoscope sheath may also be prevented from properly cleaning the distal viewing end of the endoscope. Some examples of endoscope sheaths can be found in U.S. Pat. Nos. 7,811,228, 5,554,112 and 5,797,836 and in U.S. Pat. Pubs. 2013/0205936 and 2002/0120180, all of which are incorporated by reference herein in their entirety for all purposes.

Because endoscopes may be provided in various lengths for accommodating various medical procedures and/or because of length tolerance variations from the manufacturing processes of endoscopes and endoscope sheaths, large inventories of endoscope sheaths having various lengths may be required to ensure proper axial alignment with the distal viewing end of an endoscope. Accordingly, it may be desirable to have an endoscope sheath that can engage an endoscope and then be adjusted to axially align the distal end of the endoscope sheath with the distal viewing end of the endoscope. It may also be desirable to provide a method for axially aligning an endoscope sheath with an endoscope to accommodate endoscope sheaths and endoscopes of varying lengths.

SUMMARY

The teachings herein provide an endoscope sheath comprising a sheath tube extending along a longitudinal axis between a proximal end and a distal end, the sheath tube configured to receive at least a portion of an endoscope; a hub adapter connected to the sheath tube, the hub adapter including an arm configured to engage at least a portion of the endoscope so that the hub adapter and the sheath tube are restricted from rotating about the longitudinal axis; and a knob configured to engage a shoulder of the endoscope and the sheath tube so that movement of the knob relative to the hub adapter moves the sheath tube axially along the longitudinal axis.

The teachings herein also provide a method comprising providing a sheath tube extending along a longitudinal axis between a proximal end and a distal end; providing an endoscope having a proximal end, a distal end and a shoulder disposed there between; providing a knob between the proximal end of the sheath tube and the shoulder; engaging a distal end of the knob with the proximal end of the sheath tube; inserting at least a portion of the endoscope through a through bore in the knob and into the sheath tube; and rotating the knob in a first direction, a second direction, or both relative to the longitudinal axis of the sheath tube so that the distal end of the sheath tube moves along the longitudinal axis.

The teachings herein further provide an endoscope sheath that can be quickly adjusted to custom fit endoscopes of varying lengths.

Further yet, the teachings provide a method for axially aligning an endoscope sheath to an endoscope to accommodate endoscope sheaths, endoscopes, or both having various lengths.

DETAILED DESCRIPTION

Figure 1:
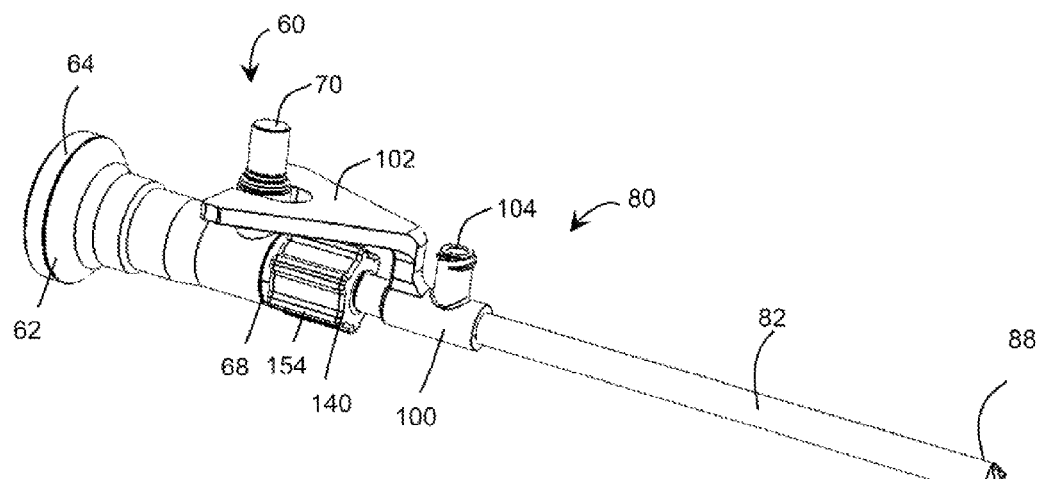
FIG. 1 illustrates a perspective view of an endoscope connected to a knob, a hub adapter, and an endoscope sheath in accordance with the teachings herein.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings provide a system and an endoscope sheath for use with an endoscope. The system may function to clean and protect an endoscope sheath, an endoscope, or both. The system may function to clean and protect a distal end of an endoscope. The system may function to clean an image sensor, a lens, or a device located at a distal viewing end of an endoscope. The system may include one or more irrigation sources supplying an irrigation fluid to an endoscope sheath, an endoscope, a distal viewing end of an endoscope, or a combination thereof, and one or more suction sources pulling suction from an endoscope sheath, an endoscope, a distal viewing end of an endoscope, or a combination thereof. The one or more irrigation sources, suction sources, or both may be in constant communication, selective communication, or both with an endoscope sheath, an endoscope, a distal viewing end of an endoscope, or a combination thereof. The system may include one or more control modules that may function to control the one or more irrigation sources, suction sources, endoscope sheaths, endoscopes, or a combination thereof.

The one or more control modules may function to control an amount of irrigation fluid, suction, or both supplied, applied, or pulled to/from an endoscope sheath, an endoscope, a distal viewing end of an endoscope, an area or location of interest, a surgical site, or a combination thereof. The one or more control modules may control a running speed, pumping duration, or both of the one or more pumps supplying irrigation fluid. The one or more control modules may control an order of application of irrigation fluid, suction, or both. The one or more control modules may function to stop a flow of irrigation fluid or suction, apply a flow of irrigation fluid or suction, or a combination thereof. The one or more control modules may include a power source, which may be electricity, battery, or both. The one or more control modules may include a microprocessor, a computer, a control algorithm, or a combination thereof. The one or more control modules may include one or more user interfaces, one or more pumps, one or more valves, or a combination thereof.

The one or more user interfaces may function to provide a user, such as a surgeon, doctor, or nurse, with the ability to monitor and/or control the system. The user interface may include one or more control knobs, buttons, switches, or selectors; one or more indicators; one or more user controls; one or more devices for adjusting, changing, or setting a system parameter or function; or a combination thereof. During use, for example, a user may activate, adjust, or both one or more of the control knobs, buttons, indicators, controls, etc. to activate, control, adjust or a combination thereof one or more pumps, valves, system functions, or a combination thereof to start, stop, or change a system function, such as an irrigation function, a suction function, or application cycle.

The one or more pumps may function to supply, circulate, or move irrigation fluid from an irrigation source to a control module, an endoscope sheath, an endoscope, a distal viewing end of an endoscope, or a combination thereof. The pump may supply, circulate, or move irrigation fluid with an impeller. The pump may function to create a negative pressure (e.g., suction or vacuum). Preferably, when the pump is activated, an amount of irrigation fluid is moved, which, during use, may be constant or may selectively vary. The pump may be a lobe pump, a centrifugal pump, a positive displacement pump, a rotary positive displacement pump, a diaphragm pump, a peristaltic pump, a rope pump, a gear pump, a screw pump, a progressing cavity pump, a roots-type pump, a plunger pump, or a combination thereof. Preferably, the pump is a peristaltic pump for supplying irrigation fluid through one or more irrigation lines.

The irrigation fluid may function to clean an endoscope sheath, an endoscope a distal viewing end of an endoscope, or a combination thereof. The irrigation fluid may function to move or flush particles, opaque fluids, contaminants, cut biological tissue, blood, obstructions, etc. or a combination thereof from an endoscope sheath, an endoscope, a distal viewing end of an endoscope, a surgical site, or a combination thereof. The irrigation fluid may function to clean an image sensor, lens or device of an endoscope while the endoscope and endoscope sheath is in a patient. The irrigation fluid may be bioabsorbable. During an application cycle, the irrigation fluid may be applied continuously, selectively, intermittingly, on-demand, or a combination thereof. The irrigation fluid may be supplied with a pump configured to pump the irrigation fluid at a pressure. The pressure of the irrigation fluid may change as the irrigation fluid reaches a distal end of an endoscope sheath, an endoscope, a distal viewing end of an endoscope, or a combination thereof. The irrigation fluid may be supplied via a gravity feed, and thus, the pressure of the irrigation fluid may be determined by the height of an irrigation source. For example, a vertical placement height of an irrigation source may determine the amount of pressure and/or force the irrigation fluid applies to a distal end of an endoscope sheath, an endoscope, a distal viewing end of an endoscope, or a combination thereof. It may be desirable that the pressure of the irrigation fluid is sufficiently high so that a flow director may redirect the irrigation fluid. The flow director may be located at a distal end of the endoscope sheath. The irrigation fluid may be applied with a sufficient amount of pressure so that the surface tension of the irrigation fluid wicks across a distal end of an endoscope sheath, an endoscope, a distal viewing end of an endoscope, or a combination thereof (e.g., the pressure may be low enough that the irrigation fluid remains in contact with an endoscope sheath, an endoscope, or both). Preferably, the pressure is low so that the flow of irrigation fluid is laminar across an endoscope sheath, an endoscope, an image sensor, lens or device, or combination thereof. The irrigation fluid may be applied with a pressure of about 0.10 MPa or more, about 0.20 MPa or more, about 0.30 MPa or more, or even about 0.50 MPa or more. The irrigation fluid may be applied with a pressure of about 3 MPa or less, about 2 MPa or less, about 1 MPa or less, or even about 0.75 MPa or less. The pressure of the irrigation fluid may be varied based on a size, length, or both of an irrigation line extending between an irrigation source and an endoscope sheath, an endoscope, a distal viewing end of an endoscope, or a combination thereof.

The one or more irrigation lines may function to connect an irrigation source to an endoscope sheath, endoscope, or both. The one or more irrigation lines may be one or any number of lines supplying irrigation fluid to an endoscope sheath, endoscope, or both. The one or more irrigation lines may function to assist in creating a pressure head so that the irrigation fluid is supplied, applied, transferred, moved, or a combination thereof to move, remove, or flush particles, opaque fluids, contaminants, cut biological tissue, blood, obstructions, or a combination thereof from a point of interest, an endoscope sheath, an endoscope, a distal viewing end of an endoscope, a surgical site, or from a combination thereof. The one or more irrigation lines may be elongated, rigid, flexible, or movable tubes or conduits, or a combination thereof. The one or more irrigation lines may be made of a material suitable for use in surgical procedures. The one or more irrigation lines may also connect a suction source to an endoscope sheath, an endoscope, or both (i.e., suction may be supplied through the irrigation lines).

The suction source may function to move, remove, or flush particles, opaque fluids, contaminants, cut biological tissue, blood, obstructions, or a combination thereof from a point of interest, an endoscope sheath, an endoscope, a distal viewing end of an endoscope, a surgical site, or from a combination thereof. The suction source may function to perform a drying function, remove fluid spots, remove contaminants, or a combination thereof. The suction source may be a pump, reversal of a motor, a common suction source, a hospital suction source, or a combination thereof. The suction source may be configured to pull a sufficient amount of vacuum through one or more suction lines, irrigation lines, or both to remove a predetermined amount of fluid in a predetermined amount of time. For example, the suction source may pull suction so that 10 ml of irrigation fluid is removed in 1 to 2 seconds. The suction source may pull suction that is continuous, selective, on-demand, or a combination thereof through one or more suction lines.

The one or more suction lines may function to connect a suction source to an endoscope sheath, an endoscope, or both. The one or more suction lines may be one or more lines providing a conduit for suction or vacuum to be pulled by suction source from an endoscope sheath, an endoscope, a distal viewing end of an endoscope, or a combination thereof. The one or more suction lines may function to assist in pulling a vacuum at or near a distal end of an endoscope sheath, an endoscope, a distal viewing end of an endoscope, or a combination thereof. The one or more suction lines may be elongated, rigid, flexible, movable tubes conduits, or a combination thereof. The one or more suction lines may be made of a material suitable for use in surgical procedures to pull vacuum or suction. The one or more suction lines may also connect an irrigation source to an endoscope sheath, an endoscope, or both (i.e., irrigation may be supplied through the suction lines). The suction lines and the irrigation lines may be the same line or may be different lines. The suction line, the irrigation line, or both may include one or more valves, fittings, or both.

The one or more valves may function to allow either a suction function or an irrigation function to work at a given time. For example, the one or more valves may function to block one or more of the irrigation lines or one or more of the suction lines so that only suction or only irrigation fluid, respectively, is applied at a given time. The one or more valves may be a check valve, a back flow preventer, or both. The one or more valves may be located proximate to an endoscope sheath, an endoscope, an irrigation source, a suction source, a control module, or a combination thereof. If more than one valve is present, the valves may be connected electrically, hydraulically, fluidly, or in a combination thereof. For example, when one valve is opened another valve can be closed. If two or more valves are present, the valves may be operated in a sequence (e.g., one valve opens and closes before another valve opens); operated simultaneously (e.g. both valves open at the same time); operated on a delay (e.g. one valve opens or closes before another valve opens or closes); or in any combination thereof. The one or more valves may be part of, or in communication with, a common fitting, located proximate to a common fitting, or both.

The one or more common fittings may function to connect one or more suction lines, irrigation lines, or both to a common line. The one or more common fittings may function to provide suction and irrigation fluid to an endoscope sheath, endoscope, or both through a single port on the endoscopes sheath or endoscope. For example, the common fitting may connect a suction line and an irrigation line to a common line that is connected to an endoscope sheath so that irrigation fluid can be supplied to the endoscope sheath and after the irrigation fluid is supplied, suction may be applied through the same line. The one or more common fittings may connect a one or more suction lines, irrigation lines, or both, to multiple devices so that the multiple devices may be used simultaneously, in series, in parallel, or in a combined use. The one or more common fittings may include two or more openings, three or more openings, four or more openings, or five or more openings. Each opening may receive one or more suction lines, one or more irrigation lines, or both and may fluidly connect the one or more lines together. More than one common fitting may be used to connect multiple lines together. For example, a first common fitting with three openings may be connected to a second common fitting with three openings so that two lines are connected to one opening of the first common fitting and one tube is connected to each of the other two openings. Preferably, the common fitting is generally "Y" shaped and two of the openings lead into a third opening that is connected to one or more commons line and/or one or more delivery lines.

The one or more common lines and/or one or more delivery lines may function to deliver, supply, apply, remove or a combination thereof irrigation fluid, suction, or both to an endoscope sheath, an endoscope, or both. The common line may function to provide a combination of multiple different fluids, devices, suction levels, fluid pressures, or a combination thereof. The common line may provide a single access point between an irrigation source, a suction source, a control module, or a combination thereof and an endoscope sheath, an endoscope, or both. The common line may have an increased cross-sectional area (e.g., diameter) relative to a cross-sectional area of an irrigation line, a suction line, or both. The common line may be the same size as the irrigation lines, suction lines, or both. The common line may extend between a common fitting and a port of an endoscope sheath, an endoscope, or both. The common line may function to deliver one or more fluids to an endoscope sheath, an endoscope, or both during an application cycle.

The application cycle may function to clean, protect or both an endoscope sheath, an endoscope, a distal viewing end of an endoscope, an area or location of interest, a surgical site, or a combination thereof. The application cycle may function to clean an imaging lens or device associated with or located at a distal viewing end of an endoscope. The application cycle may be sufficiently long so that an image sensor, a lens or device of an endoscope, a distal viewing end of an endoscope, or a combination thereof can be cleaned and good images can be obtained therewith. The application cycle may be a cycle where a one or a combination of different applications, cycles, sequences, and/or functions are applied or performed. The application cycle may be a cycle where irrigation fluid and suction are applied simultaneously, in sequence, intermittingly, on-demand, or in a combination thereof, to clean, protect or both an endoscope sheath, an endoscope, a distal viewing end of an endoscope, or a combination thereof. For example, an application cycle may include an application of irrigation fluid followed immediately by an application of suction. The application cycle may apply a concurrent application of irrigation fluid and suction. The application cycle may include only an application of irrigation fluid (i.e., a flushing cycle, a washing manner, etc.) with no suction. The application cycle may include only an application of suction with no application of irrigation fluid. The application cycle may be varied, adjusted, monitored, and/or controlled by a user, by one or more control modules, user interfaces, or a combination thereof. For example, a user may pre-set an application cycle so that one touch of a switch causes irrigation fluid to run for 5 seconds.

The endoscope may function to provide a surgeon, a doctor, a nurse, or other interested persons with visual access into a remote location, such as an internal location of a patient. The endoscope may be used in non-invasive surgery. The endoscope may be used for orthoscopic surgery. The endoscope may be inserted into an incision in tissue. The endoscope may be inserted into an orifice, such as an ear, nose, throat, rectum, or urethra. The endoscope may have a generally circular cross section. The endoscope may include a tubular section that is generally elongated and generally cylindrical. The tubular section may extend along a longitudinal axis toward a distal viewing end. The endoscope may include a hand piece extending toward a proximal end of the endoscope. The hand piece may include a shoulder engaging a knob. The hand piece may be gripped by a user. The tubular section may be inserted into an endoscope sheath, a sheath tube, or both. The tubular section may include one or more image sensors, lenses, or devices. The one or more image sensors, lenses, or devices may be located at a distal viewing end of the endoscope. The one or more image sensors, lenses, or devices may function to provide images that are black and white, color, thermal, or a combination thereof. The one or more image sensors, lenses, or devices may be located at an angle. For example, the angle of the one or more image sensors, lenses, or devices may be about 0°, 20°, 30°, 45°, 60°, 70°, or a combination thereof. The endoscope may include a distal end, a distal viewing end, or both.

The distal viewing end may be the distal end of the endoscope, the tubular section, or both may be inserted into an incision in the tissue of a patient, a naturally occurring orifice, or both so that a feature of interest can be viewed using a minimally invasive means. Accordingly, the distal viewing end of the endoscope may be the leading portion of the endoscope (i.e., the first portion entering a patient). The distal viewing end of the endoscope may include the one or more image sensors, lenses, or devices. The distal viewing end of the endoscope may include a viewing cone or an area extending outwardly therefrom for viewing an area or location of interest. The distal viewing end may be moveable, variable, adjustable, or a combination thereof. The distal viewing end of the endoscope may be configured to be axially aligned with a distal end of an endoscope sheath, a sheath tube tip, or both. The distal end of the endoscope may oppose a proximal end of the endoscope.

The proximal end of the endoscope may function to be held or gripped by a user. The proximal end of the endoscope may function to provide controls to a doctor, a surgeon, a nurse, or other interested persons. The proximal end of the endoscope may function to provide power controls, sensing controls, irrigation controls, suction controls, a connection point to/for outside devices, or a combination thereof. The proximal end of the endoscope may provide an interface for connecting other functional components to the endoscope, such as an imaging device (e.g., a camera). The proximal end of the endoscope may include a hand piece. During use, the proximal end of the endoscope may be retained out of a patient while a distal end of the endoscope is in the patent. The proximal end of the endoscope may include a visual port.

The visual port may function to provide a viewing area or window for observing a feature of interest located at or near a distal viewing end of the endoscope. The visual port may be an optical window. The visual port may function to provide an output so that an image can be displayed on a monitor. The visual port may include a connector or a plug for connecting to a display monitor. The visual port may be integrally formed with the endoscope. The visual port may be removeably coupled to the proximal end of the endoscope via a threaded engagement. A shoulder may be located between the proximal and distal ends of the endoscope.

The shoulder may function to prevent a proximal end of the endoscope from entering a patient. The shoulder may be a distal or terminal portion of a proximal end of the endoscope, a hand piece, or both. The shoulder may be generally vertical, generally flat, or generally orthogonal relative to a longitudinal axis of a sheath tube. Once an endoscope is at least partially received into an endoscope sheath, the shoulder may function to restrict or prevent the sheath tube from moving towards a proximal end of the endoscope. The shoulder may function to form a connection with an endoscope sheath, a knob, or both. The shoulder may include an undercut, one or more ribs, a projection, or a combination thereof engaging a knob. The shoulder may include a flange including one or more ribs.

The one or more ribs may extend at least partially around the flange. The one or more ribs may extend circumferentially and continuously around the flange, intermittently around the flange, or both. The one or more ribs may extend or project from a shoulder of the endoscope. The one or more ribs may engage a knob. The one or more ribs may removeably engage a knob. The one or more ribs may provide for the knob to rotate about a longitudinal axis of a sheath tube in a first direction, a second direction, or both. The one or more ribs may engage the knob and restrict the knob from moving axially along a longitudinal axis of a sheath tube. One or more light posts may be located between the shoulder and a proximal end of the endoscope.

The one or more light posts may function to direct or provide light from a light source to, or into an endoscope, an endoscope sheath, or both so that a feature of interest located at or near a distal viewing end of an endoscope can be illuminated. The one or more light posts may include a plug or a connector for connecting a light source. The light source may be a light waveguide, an optical illuminator, a fiber optic, or a combination thereof. The one or more light posts may project or extend from the endoscope upwardly, downwardly, or in a direction there between relative to a longitudinal axis of the endoscope. The one or more light posts may be integrally formed with the endoscope. The one or more light posts may be connected to the endoscope. The one or more light posts may be made of metal, plastic, a biocompatible material, or a combination thereof. The one or more light posts may be configured to be engaged by the endoscope sheath. The one or more light posts may be engaged by an arm of an endoscope sheath, an arm of a hub adapter, or both. The one or more light posts may include a recess to be engaged by an arm, a yoke, or both. The one or more light posts may be engaged by an arm, a yoke, or both to help restrict or prevent rotation of a hub adapter, a sheath tube, or both relative to a longitudinal axis of the sheath tube.

The endoscope sheath may function provide one or more conduits, lumen, channels, or a combination thereof, for irrigation devices, suction devices, surgical tools, other functional device (e.g., a cutting tool, cauterizing tool, or both) or a combination thereof to extend into or out of a distal end of thereof. The endoscope sheath may function to provide protective functions, cleaning functions, washing functions, or a combination thereof to an endoscope, a surgical tool or device, a functional device, or a combination thereof. The endoscope sheath may function to clean and protect a distal viewing end of an endoscope. The endoscope sheath may include a sheath tube.

The sheath tube may function to clean and protect an endoscope. The sheath tube may create one or more conduits for providing irrigation fluid, suction, or both to a distal end of the endoscope. The sheath tube may function to receive, engage, protect, clean, or a combination thereof a distal viewing end of an endoscope. The sheath tube may include one or more through holes or bores extending along a longitudinal axis between a proximal end and a distal end. The sheath tube may be fabricated from a material suitable for use in medical procedures. The sheath tube may include one or more positioning devices. The sheath tube may be generally the same size and shape as an endoscope, a tubular section of an endoscope, or both, or slightly larger. For example, if tubular section of an endoscope has a generally circular cross section, then the sheath tube may also have a generally circular cross section. The sheath tube may have a shape that is different from an endoscope. The sheath tube may be any shape configured to receive, engage, support, or a combination thereof an endoscope, one or more irrigation devices, one or more suction devices, one or more surgical tools or devices, one or more other functional devices, or a combination thereof. The sheath tube may have a uniform wall thickness, a variable wall thickness, or both. The sheath tube may function to locate, support, position, or a combination thereof an endoscope, a distal viewing end of an endoscope, one or more irrigation devices, one or more suction devices, one or more surgical tools, one or more other functional device, or a combination thereof. The sheath tube may include one or more positioning devices. The one or more positioning devices may position an endoscope within the sheath tube so that the endoscope and the sheath tube are concentric, or offset. The sheath tube may be selectively moved and adjusted relative to the shoulder of the endoscope. The sheath tube may be selectively moved axially along a longitudinal axis so that the sheath tube tip located at a distal end of the sheath tube can be aligned with a distal viewing end of the endoscope.

The sheath tube tip may be the distal end of the sheath tube. The sheath tube tip may function to engage an endoscope, a distal end of an endoscope, a lens or imaging device, or a combination thereof. The sheath tube tip may function to direct irrigation fluid, suction, or both, across a distal end of an endoscope sheath, a distal viewing end of an endoscope, or both. The sheath tube tip may act as a distal end stop so that a distal viewing end of an endoscope is restricted or prevented from passing through the distal end of the endoscope sheath. The sheath tube tip may be open, or may function to selectively open, remain open, or both so that irrigation fluid can exit the sheath tube. The sheath tube tip may be configured to not interfere with imaging capabilities of the endoscope. The sheath tube tip may function to direct a viewing cone of an endoscope. The sheath tube tip may include an angled tip. The sheath tube tip may extend from a distal end of the sheath tube at an angle that substantially matches an angle of a viewing cone. For example, the sheath tube tip may include an angle on the order of 30-degrees, 45-degrees, 90-degrees, etc. The sheath tube may be selectively moved so that the sheath tube tip can be axially aligned with the distal viewing end of the endoscope. A proximal end may be located opposite the distal end, the sheath tube tip, or both of the sheath tube.

The proximal end of the sheath tube may function to engage or connect with a knob. The proximal end of the sheath tube may include a threaded portion (i.e., the second threaded portion) engaging a mating threaded portion (i.e., the first threaded portion) disposed within the knob. The proximal end of the sheath tube may be connected to a hub adapter, or the hub adapter may be formed with the sheath tube near the proximal end. A hub may be fixedly connected or removeably connected to the sheath tube with one or more mechanical fasteners, such as adhesives, threads, snap fits, one or two-way connection systems, a series of ribs, or a combination thereof. The hub may be over molded over a proximal end of a sheath tube or integrally formed therewith. The hub may include a threaded portion (i.e., the second threaded portion) engaging a mating threaded portion (i.e., the first threaded portion) disposed within the knob.

The knob may function to be rotated to move the sheath tube axially along a longitudinal axis of the sheath tube relative to a distal viewing end of an endoscope, a shoulder of an endoscope, or both. The knob may include a through bore. At least a portion of the endoscope, the tubular portion, or both may be received through the through bore when the endoscope is inserted into the sheath tube. A proximal end of the knob may include a flange. The flange may include a face that may be angled or orthogonal relative to a longitudinal axis of the sheath tube. The face may be configured to engage the shoulder. The face may abut the shoulder. The knob may include a first threaded portion disposed at least partially within the through bore near a distal end or a distal section of the knob. The first threaded portion may threadably engage a mating second threaded portion disposed on the hub, a proximal end of the sheath tube, or both. A smooth or non-threaded portion may be disposed at least partially within the through bore near a proximal end or a proximal section of the knob. The through bore may include one or more projections which may include one or more slots or cutouts cooperating to form a channel within the through hole, the flange or both. The slots or cutouts may be formed by piercing or folding at least a portion of the knob, the flange, or both downwardly toward the through hole. The channel may extend circumferentially around the through bore. The channel may be configured to engage the one or more ribs located on the shoulder of the endoscope, on the flange of the endoscope, or both. The channel may be configured so that the knob removably engages the one or more ribs. The engagement between the channel and the ribs may provide for the knob to rotate about a longitudinal axis the sheath tube. The engagement between the channel and the ribs may restrict the knob from moving axially along a longitudinal axis the sheath tube. The knob may include one or more gripping ribs on an outer surface or potion thereof. The one or more gripping ribs may extend generally parallel to a longitudinal axis of the sheath tube. The one or more gripping ribs may be gripped by a user to rotate the knob in a first direction, a second direction, or both.

Rotating the knob in the first direction, the second direction, or both may cause the sheath tube to move. Rotating the knob in the first direction, the second direction, or both may cause the second threaded portion of the sheath tube, the hub, or both to move within the first threaded portion of the knob either towards or away from the shoulder of the endoscope. Accordingly, rotating the knob in one of the directions may cause the sheath tube tip to move relative to a distal viewing end of the endoscope. When the knob is rotated in the first direction, the second direction, or both and the sheath tube moves, the endoscope may not move. The sheath tube tip may be axially aligned with the distal viewing end by rotating the knob in the first direction, the second direction, or both. A hub adapter may restrict the endoscope sheath from rotating when the knob is rotated.

The hub adapter may function to restrict or prevent the sheath tube from rotating. The hub adapter may engage at least a portion of the sheath tube and engage at least a portion of the endoscope and may form a connection there between. The hub adapter may be integrally formed with the sheath tube or may be mechanically connected thereto. The hub adapter and the sheath tube may axially move together relative to a longitudinal axis of the sheath tube when the knob is rotated, and both may be restricted from rotating when knob is rotated. The hub adapter may include a through bore for receiving at least a portion of the sheath tube. The through bore may include positioning devices such as dimples or slots that may engage one or more corresponding and mating features on the sheath tube to prevent the sheath tube from rotating. The through bore may engage at least a portion of the sheath tube with an interference fit so that the endoscope sheath and the hub adapter move axially together relative to a shoulder of the endoscope when the knob is rotated. The hub adapter may allow for the sheath tube to move axially relative to a longitudinal axis of the sheath tube when the knob is rotated, without moving the hub adapter. The hub adapter may include one or more arms engaging the light post of the endoscope.

The one or more arms may function to prevent rotation of the sheath tube, the hub adapter or both relative to the endoscope. The one or more arms may cantilever from the hub adapter. The one or more arms may engage an endoscope, a light post of an endoscope or both. The one or more arms include a yoke engaging the light post. The yoke may include a slot allowing axial movement of the sheath tube and the hub adapter along a longitudinal axis of the sheath tube. The one or more arms, the yoke, or both may engage the light post so that the sheath tube can axially move along a longitudinal axis of the sheath tube, while the hub adapter is restricted from moving. A port may be located next to the one or more arms on the hub adapter.

The port of the hub adapter may function to receive irrigation fluid, suction, or both from an irrigation source, a suction source, a control module, or a combination thereof. The port may function to direct irrigation fluid, section, or both to an endoscope, a distal viewing end of an endoscope, a sheath tube, or a combination thereof. The port may be configured to engage a common line, a common fitting, a valve, or combination thereof to selectively supply irrigation food, section, or both to the hub adapter, the endoscope sheath, the endoscope, or a combination thereof.

FIG. 1 illustrates an endoscope 60 inserted into an endoscope sheath 80. At a proximal end 64, the endoscope 60 includes a visual port 62 for viewing a feature of interest located at or near a distal viewing end 66 of the endoscope 60. The endoscope 60 includes a shoulder 68 located between the proximal and distal ends 64, 66. A light post 70 for connecting illumination to the endoscope 60 is located between the proximal end 64 and the shoulder 68. The endoscope sheath 80 includes a sheath tube 82 including a sheath tube tip 88 at a distal end 86 thereof. The sheath tube 82 receives at least a portion of the endoscope 60 therein. A hub adapter 100 engages at least a portion of the sheath tube 82 and includes an arm 102 engaging the light post 70 of the endoscope 60 preventing rotation of the hub adapter 100 and the sheath tube 82. The hub adapter 100 includes a port 104 receiving irrigation fluid, suction, or both. A rotatable knob 140 is located between the hub adapter 100 and the shoulder 68. The knob 140 includes one or more gripping ribs 154.

Figure 2:
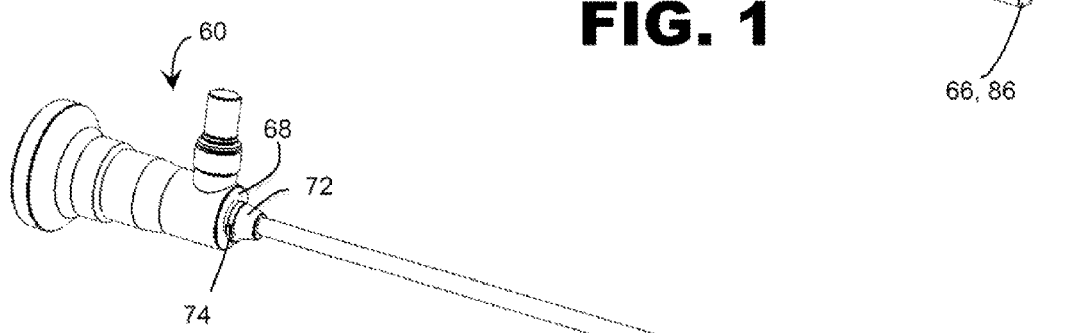
FIG. 2 illustrates an exploded perspective view of an endoscope, a knob, a hub, a hub adapter, and an endoscope sheath in accordance with the teachings herein.
Figure 2:
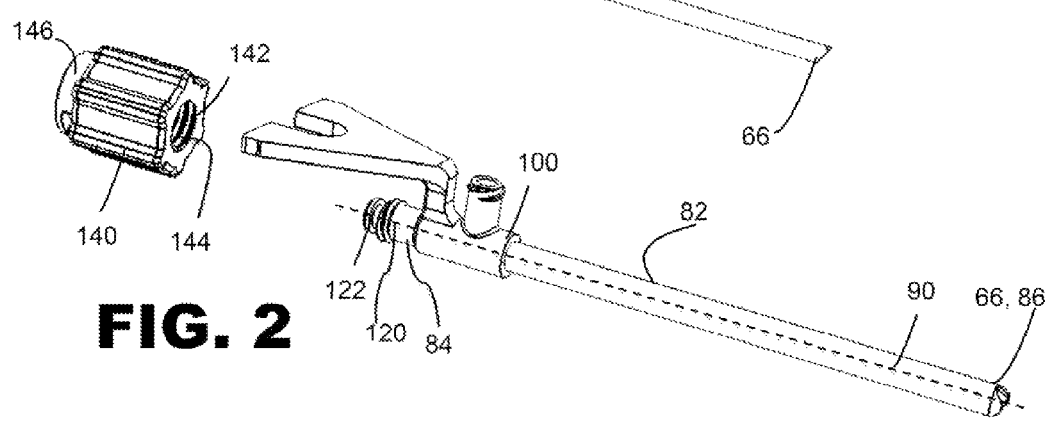

FIG. 2 illustrates an endoscope 60 including similar features identified in FIG. 1. The shoulder 68 includes a flange 72. The flange 72 includes a rib 74 at least partially disposed therearound. The knob 140 includes a through bore 142, and at least a portion of the through bore 142 includes a first threaded portion 144. The knob 140 includes a flange 146. A hub 120 is located at a proximal end 84 of the sheath tube 82. The hub 120 includes a second threaded portion 122 for engaging the first threaded portion 144 of the knob 140. The hub adapter 100 engages at least a portion of the sheath tube 82. The sheath tube 82 extends along a longitudinal axis 90.

Figure 3:
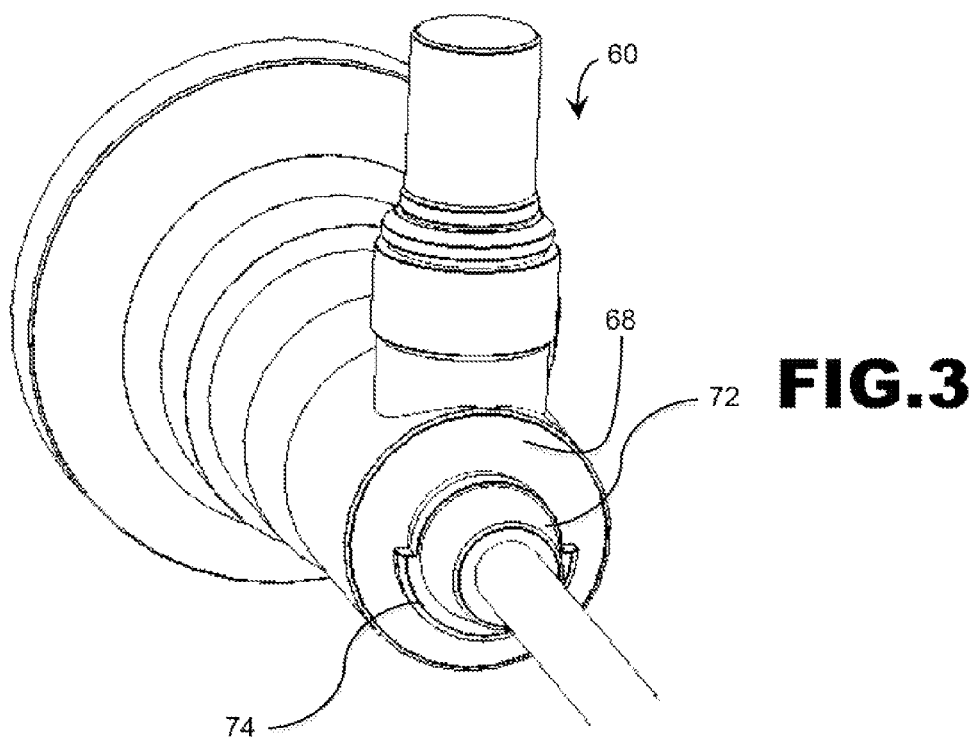
FIG. 3 illustrates a partial perspective view of an endoscope in accordance with the teachings herein.

FIG. 3 illustrates another view of a portion of the endoscope 60 showing the shoulder 68 and the rib 74 on the flange 72.

Figure 4:
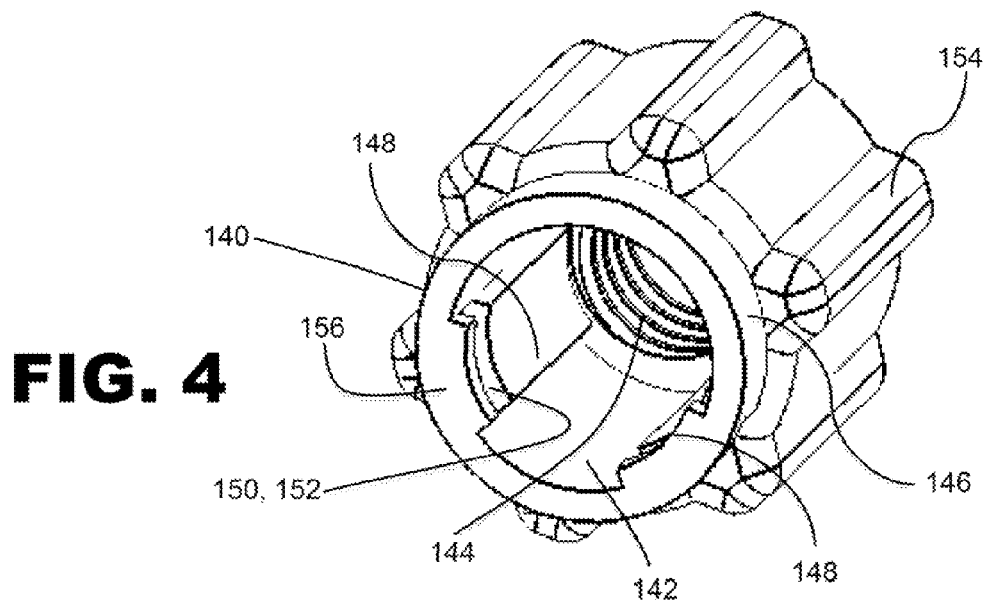
FIG. 4 illustrates a perspective view of an knob in accordance with the teachings herein.

FIG. 4 illustrates another view of the knob 140. The through bore 142 extends through the entire length of the knob 140 and near the distal end thereof includes the first threaded portion 144. The first threaded portion 144 threadably engages the second threaded portion 122 of the hub 120. Within the through bore 142, the knob 140 includes a pair of projections 148. Each projection 148 includes a cutout 150 cooperating together to form a generally circumferential channel 152 within the through bore 142. The channel 152 rotationally engages the rib 74 of the endoscope 60 so that the knob 140 can rotate about the longitudinal axis 90 of the sheath tube 82 but restricted from moving axially along the longitudinal axis 90. The flange 146 includes a face 156 abutting the shoulder 68 of the endoscope 60.

With reference to FIGS. 1-4, the arm 102 of the hub adapter 100 engages the light post 70 of endoscope 60 to prevent rotation of the hub adapter 100 and the sheath tube 82 about the longitudinal axis 90. The knob 140 can be rotated about the longitudinal axis 90 in a first direction or in a second direction. Rotating the knob 140 causes the second threaded portion 122 to move along the first threaded portion 144 of the knob 140. As the second threaded portion 122 moves along the first threaded portion 144, the sheath tube 82 correspondingly moves axially along the longitudinal axis 90. Accordingly, a user can grip one of the gripping ribs 154 and rotate the knob 140 in the first direction or the second direction to axially move the sheath tube tip 88 towards or away from the distal viewing end 66 of the endoscope 60 to axially align the endoscope sheath 80 and the endoscope 60.

Figure 5:
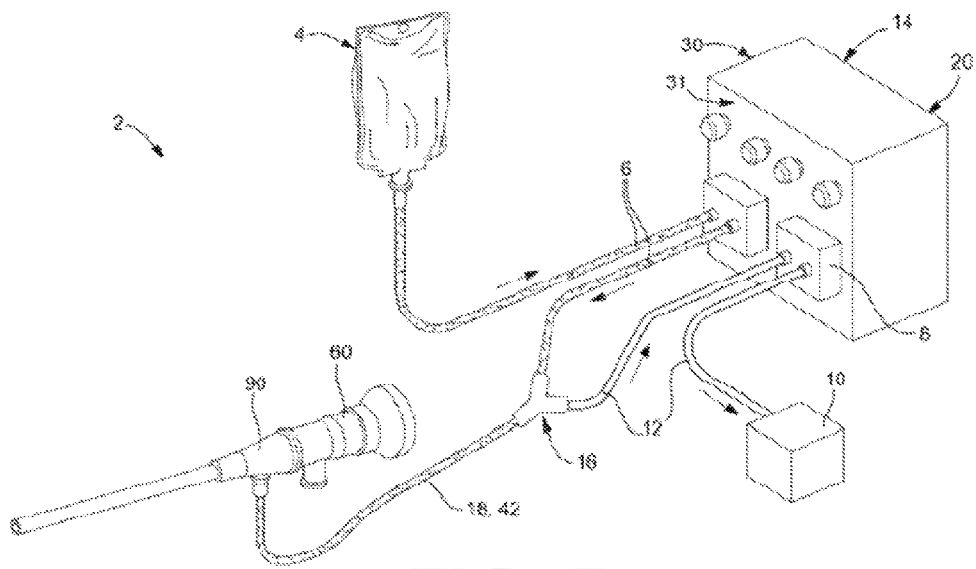
FIG. 5 illustrates a system for use with an endoscope and an endoscope sheath of the teachings herein in accordance with the teachings herein.
Figure 6:
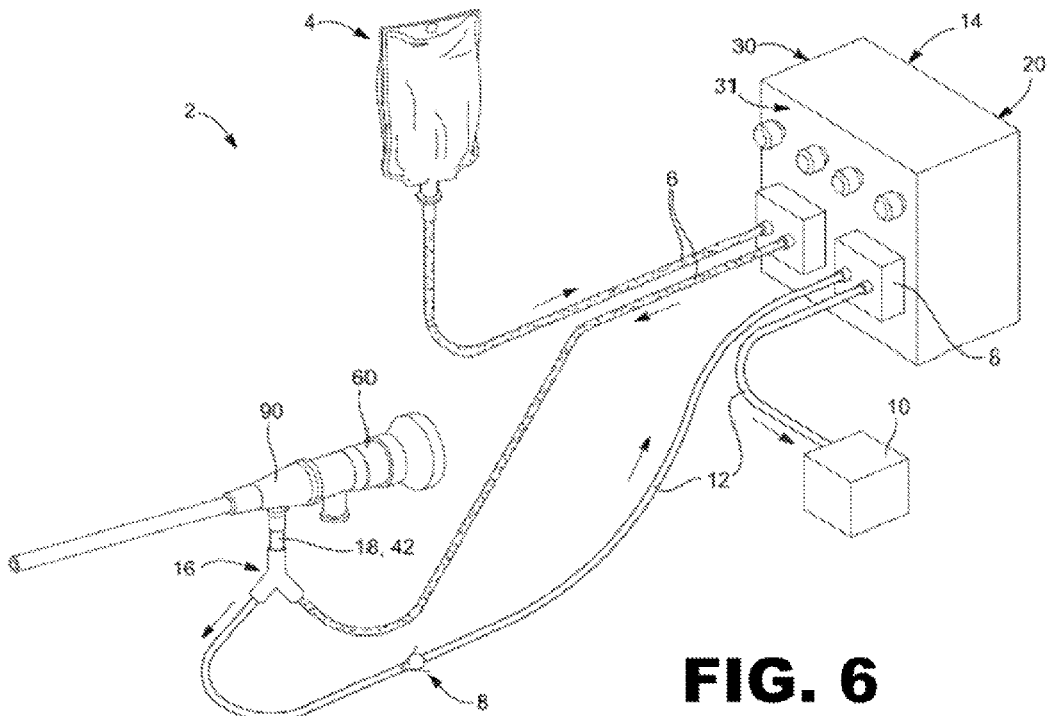
FIG. 6 illustrates a system for use with an endoscope and an endoscope sheath of the teachings herein in accordance with the teachings herein.

FIGS. 5 and 6 illustrate an endoscope cleaning system 2. The endoscope cleaning system 2 includes an irrigation source 4 and a suction source 10. The irrigation source 4 and the suction source 10 are in communication with a control module 30 via an irrigation line 6 and a suction line 12, respectively. The control module 30 includes a pump 14 controlling a flow of irrigation fluid between the irrigation source 4 and an endoscope sheath 90. The control module 30 includes a valve 8 controlling suction between the suction source 10 and the endoscope sheath 90 so that suction can be turned off during all or portion of an application cycle of irrigation fluid. The control module 30 includes a power source 20 and a controller and/or microprocessor (not specifically illustrated) in communication with a user interface 31. The user interface 31 controls the control module 30. The irrigation line 6 and the suction line 12 are coupled together with a common fitting 16. The common fitting connects the irrigation line 6 and the suction line 12 to a common line 18/delivery line 42 to supply irrigation fluid, suction, or both to the endoscope sheath 90 for cleaning the endoscope 60.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values that are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

I claim:

1. An endoscope sheath comprising:
   a sheath tube extending along a longitudinal axis between a proximal end and a distal end, the sheath tube configured to receive at least a portion of an endoscope;
   a hub adapter connected to the sheath tube, the hub adapter including an arm configured to engage at least a portion of the endoscope so that the hub adapter and the sheath tube are restricted from rotating about the longitudinal axis; and
   a knob configured to engage a shoulder of the endoscope and the sheath tube so that movement of the knob relative to the hub adapter moves the sheath tube axially along the longitudinal axis without the endoscope axially moving along the longitudinal axis.

2. The endoscope sheath of claim 1, wherein the knob includes a first threaded portion and the proximal end of the sheath tube includes a second threaded portion engaging the first threaded portion so that movement of the knob moves the sheath tube, the hub adapter, or both axially along the longitudinal axis.

3. The endoscope sheath of claim 2, wherein the distal end of the sheath tube includes a sheath tube tip including an angled tip, wherein movement of the knob moves the sheath tube so that the sheath tube tip is configured to generally align with the distal end of the endoscope.

4. The endoscope sheath of claim 3, wherein the knob includes a through bore configured to receive at least a portion of the endoscope, the through bore includes a distal section and a proximal section, the distal section includes the first threaded portion and the proximal section includes a non-threaded section, the non-threaded section includes a channel configured to rotatably engage a rib located on a flange of the shoulder so that the knob is prevented from axially moving relative to the shoulder when the knob is rotated.

5. The endoscope sheath of claim 4, wherein the channel includes one or more slots cooperating to form the channel and the rib extends partially around the flange so that the knob is removeably rotationally engaged thereon.

6. The endoscope sheath of claim 2, wherein a hub is fixedly connected to the proximal end of the sheath tube, the hub including the second threaded portion.

7. The endoscope sheath of claim 4, wherein the rib extends around only a portion of a circumference of the flange, and
   wherein when the channel is aligned such that the rib disengages from within the channel, the knob can be separated from the endoscope.

8. The endoscope sheath of claim 1, wherein the arm of the hub adapter includes a yoke configured to engage a light post on the endoscope so that the hub adapter and the endoscope sheath are both restricted from rotating relative to the shoulder.

9. The endoscope sheath of claim 8, wherein the yoke includes a slot so that the hub adapter can move axially along the longitudinal axis with the sheath tube when the knob is moved.

10. The endoscope sheath of claim 9, wherein the hub adapter includes a port for supplying irrigation fluid, suction, or both to the endoscope sheath, the endoscope, or both.

11. A method comprising:
    providing a sheath tube extending along a longitudinal axis between a proximal end and a distal end;
    providing an endoscope having a proximal end, a distal end and a shoulder disposed there between;
    providing a knob between the proximal end of the sheath tube and the shoulder;
    engaging a distal end of the knob with the proximal end of the sheath tube;
    inserting at least a portion of the endoscope through a through bore in the knob and into the sheath tube; and
    rotating the knob in a first direction, a second direction, or both relative to the longitudinal axis of the sheath tube so that the distal end of the sheath tube moves along the longitudinal axis without the endoscope moving.

12. The method of claim 11, wherein the sheath tube includes an arm engaging at least a portion of the endoscope so that the sheath tube is restricted from rotating about the longitudinal axis when the knob is rotated in the first direction, the second direction, or both.

13. The method of claim 12, wherein the knob includes a first threaded portion and the sheath tube includes a second threaded portion threadably engaging the first threaded portion, the knob including a face abutting the shoulder of the endoscope,
    wherein rotating the knob in the first direction causes the distal end of the sheath tube to move axially along the longitudinal axis towards the distal end of the endoscope without the knob axially moving relative to the shoulder, and
    wherein rotating the knob in the second direction causes the distal end of the sheath tube to move axially along the longitudinal axis away from the distal end of the endoscope without the knob axially moving relative to the shoulder.

14. The method of claim 13, wherein the shoulder of the endoscope includes a rib and the knob includes a channel rotatably engaging the rib so that the knob is prevented from axially moving relative to the shoulder.

15. The method of claim 14, wherein the channel includes one or more slots cooperating to form the channel and the rib is partially disposed around a flange of the shoulder so that the knob is removeably rotationally engaged thereon.

16. The method of claim 15, wherein the method also includes:
    introducing an irrigation fluid, suction, or both from a source to a port on a hub adapter; and supplying the irrigation fluid, suction, or both to the distal end of the sheath tube so that the distal end of the endoscope can be cleaned.

17. An endoscope sheath comprising:
a sheath tube extending along a longitudinal axis, the sheath tube is configured to receive at least a portion of an endoscope, the sheath tube includes a sheath tube tip at a distal end of the sheath tube;
a hub adapter located at a proximal end of the sheath tube, the hub adapter configured to engage a portion of the endoscope so that the hub adapter and the sheath tube are restricted from rotating about the longitudinal axis; and
a knob configured to rotatably engage the endoscope and the sheath tube,
wherein rotating the knob causes the sheath tube tip to move axially along the longitudinal axis relative to a distal viewing end of the endoscope without the endoscope moving along the longitudinal axis and without the knob moving along the longitudinal axis.

18. The endoscope sheath of claim 17, wherein the knob includes a through bore configured to receive at least a portion of the endoscope, the through bore includes a distal section and a proximal section, the distal section includes a first threaded portion and the proximal section includes a non-threaded section, the non-threaded section includes a channel configured to rotatably engage a rib radially extending from a flange that axially extends from a shoulder so that the knob is prevented from axially moving relative to the shoulder of the endoscope when the knob is rotated, and
wherein when the rib disengages from within the channel, the knob can be separated from the endoscope.

19. The endoscope sheath of claim 18, wherein the knob includes a first threaded portion and a proximal end of the sheath tube includes a second threaded portion that engages the first threaded portion, and
wherein rotation of the knob causes the sheath tube and the hub adapter to move axially along the longitudinal axis without the endoscope and the knob moving along the longitudinal axis.

20. The endoscope sheath of claim 17, wherein the hub adapter includes a yoke that is configured to engage a light post on the endoscope so that the hub adapter and the endoscope sheath are both restricted from rotating relative to the longitudinal axis, and
wherein the hub adapter also includes a port for supplying irrigation fluid, suction, or both to the endoscope sheath.

* * * * *